United States Patent
Chung et al.

(10) Patent No.: US 8,592,131 B2
(45) Date of Patent: Nov. 26, 2013

(54) ORTHO-NITROBENZYL ESTER COMPOUND AND POSITIVE TYPE PHOTOSENSITIVE RESIN COMPOSITION INCLUDING THE SAME

(75) Inventors: Min-Kook Chung, Uiwang-si (KR);
Ji-Young Jeong, Uiwang-si (KR);
Hyun-Yong Cho, Uiwang-si (KR);
Yong-Sik Yoo, Uiwang-si (KR);
Jeong-Woo Lee, Uiwang-si (KR);
Jong-Hwa Lee, Uiwang-si (KR);
Hwan-Sung Cheon, Uiwang-si (KR);
Soo-Young Kim, Seongnam-si (KR);
Young-Ho Kim, Yongin-si (KR);
Jae-Hyun Kim, Yongin-si (KR); Su-Min Park, Seoul (KR)

(73) Assignee: Cheil Industries Inc., Gumi-si (KR)

( * ) Notice: Subject to any disclaimer, the term of this patent is extended or adjusted under 35 U.S.C. 154(b) by 0 days.

(21) Appl. No.: 13/239,441

(22) Filed: Sep. 22, 2011

(65) Prior Publication Data
US 2012/0156622 A1    Jun. 21, 2012

(30) Foreign Application Priority Data
Dec. 15, 2010    (KR) .................. 10-2010-0128278

(51) Int. Cl.
G03F 7/00 (2006.01)
G03F 7/004 (2006.01)
G03F 7/075 (2006.01)
C07C 69/94 (2006.01)

(52) U.S. Cl.
USPC ........ 430/270.1; 430/905; 430/910; 430/913; 430/915; 430/926; 560/61

(58) Field of Classification Search
USPC .............. 430/270.1, 905, 913, 910, 915, 926; 560/61
See application file for complete search history.

(56) References Cited

U.S. PATENT DOCUMENTS

| | | | | |
|---|---|---|---|---|
| 5,081,000 A | * | 1/1992 | Kuehn et al. | 430/281.1 |
| 5,302,488 A | * | 4/1994 | Roeschert et al. | 430/190 |
| 5,326,826 A | * | 7/1994 | Roeschert et al. | 525/326.5 |
| 5,457,003 A | * | 10/1995 | Tanaka et al. | 430/176 |
| 5,518,864 A | * | 5/1996 | Oba et al. | 430/325 |
| 5,830,619 A | | 11/1998 | Chin et al. | |
| 5,843,319 A | * | 12/1998 | Przybilla et al. | 210/668 |
| 6,646,243 B2 | | 11/2003 | Pirrung et al. | |
| 6,696,112 B2 | * | 2/2004 | Okuda et al. | 428/1.1 |
| 6,824,947 B2 | * | 11/2004 | Ishizuka et al. | 430/157 |
| 6,887,643 B2 | * | 5/2005 | Fujita et al. | 430/191 |
| 7,150,947 B2 | * | 12/2006 | Nunomura et al. | 430/18 |
| 7,301,049 B2 | | 11/2007 | Serafinowski et al. | |
| 7,479,362 B2 | | 1/2009 | Fukushima et al. | |
| 7,598,009 B2 | * | 10/2009 | Sato et al. | 430/18 |
| 7,713,677 B2 | | 5/2010 | Lee et al. | |
| 8,097,386 B2 | * | 1/2012 | Nakano et al. | 430/18 |
| 8,133,550 B2 | * | 3/2012 | Sato et al. | 427/510 |

FOREIGN PATENT DOCUMENTS

| | | |
|---|---|---|
| CN | 1480491 | 3/2004 |
| CN | 1267501 | 8/2006 |
| EP | 0249139 B2 | 3/1998 |
| JP | 10-097357 | 4/1998 |
| JP | 2001-242619 | 9/2001 |
| JP | 2010-256706 | 11/2010 |
| JP | 2010256706 A * | 11/2010 |
| KR | 10-0180973 B1 | 12/1998 |
| KR | 10-0301103 | 6/2001 |
| KR | 10-2007-0081805 A | 8/2007 |
| KR | 10-2010-0035571 A | 4/2010 |
| KR | 10-2010-0110580 A | 10/2010 |

OTHER PUBLICATIONS

Machine translation of JP 2010-256706 (no date).*
Chinese Search Report issued in counterpart Chinese Application No. 201110301200.7 on Jul. 5, 2013, pp. 1-2.
Taiwanese Search Report issued in counterpart Taiwanese Application No. 100135518 on Aug. 23, 2013, pp. 1-2.

\* cited by examiner

*Primary Examiner* — Amanda C. Walke
(74) *Attorney, Agent, or Firm* — Additon, Higgins, Pendelton & Ashe, P.A.

(57) ABSTRACT

An ortho-nitrobenzyl ester compound including a compound represented by Chemical Formula 1, and a positive photosensitive resin composition including the same are provided.

4 Claims, No Drawings

ORTHO-NITROBENZYL ESTER COMPOUND AND POSITIVE TYPE PHOTOSENSITIVE RESIN COMPOSITION INCLUDING THE SAME

CROSS-REFERENCE TO RELATED APPLICATION

This application claims priority under 35 USC Section 119 to and the benefit of Korean Patent Application No. 10-2010-0128278 filed in the Korean Intellectual Property Office on Dec. 15, 2010, the entire disclosure of which is incorporated herein by reference.

FIELD OF THE INVENTION

This disclosure relates to an ortho-nitrobenzyl ester compound and a positive photosensitive resin composition including the same.

BACKGROUND OF THE INVENTION

A conventional positive photosensitive resin composition is generally prepared by mixing a resin with a phenol-type hydroxy group easily dissolved in an alkali aqueous solution and a photosensitizer suppressing dissolution of the resin during non-exposure and promoting development of the resin or suspending the suppression of dissolution of the resin during exposure, thus making patterning of the resin possible. The resin may include a novolac resin prepared by condensation-polymerizing a phenol-based compound and formaldehyde and a poly(4-hydroxy)styrene resin, polyhydroxy amide as a polybenzoxazole precursor, and the like. The photosensitizer may include a diazonaphthoquinone compound including sulfonic acid ester and amide at the 4- or 5-position.

The positive photosensitive resin composition may have dissolution-suppressing performance depending on capability of a photosensitizer suppressing dissolution of a non-exposed part, capability of the photosensitizer easily dissolved after the exposure, and capability of recovering or promoting a dissolution rate of the resin due to the dissolution. A conventional diazonaphthoquinone compound may have excellent photodissolution rate and light absorption but not good capability of inhibiting dissolution of a non-exposed part. Accordingly, typical compositions include increased amounts of diazonaphthoquinone compound to secure an appropriate residual film ratio for patterning. The increased amount of diazonaphthoquinone compound is dissolved to pattern an exposed part, which can require a higher exposure dose and resulting relatively low sensitivity.

Therefore, there is a need for a photosensitive assistant which can inhibit dissolution of a non-exposed part.

SUMMARY OF THE INVENTION

One embodiment provides an ortho-nitrobenzyl ester compound that can have excellent dissolution inhibition capability for non-exposed parts.

Another embodiment provides a positive photosensitive resin composition including the ortho-nitrobenzyl ester compound, that can have excellent sensitivity, resolution, a pattern profile, and residue removal properties.

Yet another embodiment provides a photosensitive resin film fabricated using the positive photosensitive resin composition.

Still another embodiment provides a semiconductor device including the photosensitive resin film.

According to one embodiment, an ortho-nitrobenzyl ester compound including a compound represented by the following Chemical Formula 1 is provided.

[Chemical Formula 1]

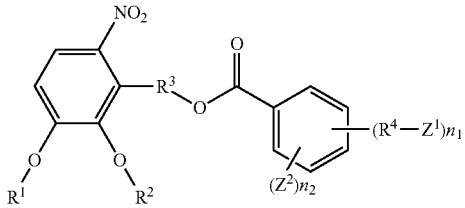

In Chemical Formula 1, $R^1$ and $R^2$ are the same or different and are each independently a substituted or unsubstituted C1 to C20 aliphatic organic group or a substituted or unsubstituted C3 to C20 alicyclic organic group, $R^3$ and $R^4$ are the same or different and are each independently a single bond or a substituted or unsubstituted divalent C1 to C20 aliphatic organic group, $Z^1$ and $Z^2$ are the same or different and are each independently hydroxy (OH), amine (N($R^{103}$)($R^{104}$), wherein $R^{103}$ and $R^{104}$ are the same or different and are each independently hydrogen or a substituted or unsubstituted aliphatic organic group), carboxyl (COOH) or aldehyde (CHO), $n_1$ and $n_2$ are the same or different and are each independently integers ranging from 0 to 5, and $n_1+n_2$ is an integer ranging from 1 to 5.

In exemplary embodiments, $Z^1$ and $Z^2$ may be the same or different and each may independently be hydroxy (OH) or carboxyl (COOH). For example, each $Z^1$ and $Z^2$ may be hydroxy (OH).

The ortho-nitrobenzyl ester compound may include a compound represented by the following Chemical Formulae 2 to 4, or a combination thereof.

[Chemical Formula 2]

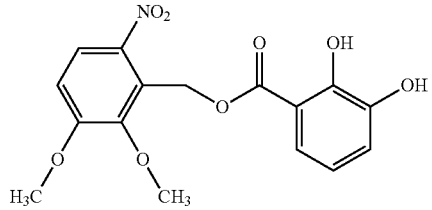

[Chemical Formula 3]

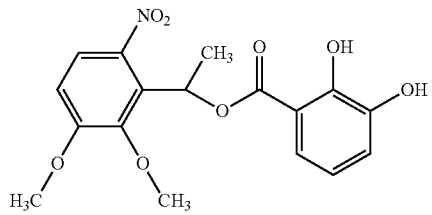

[Chemical Formula 4]

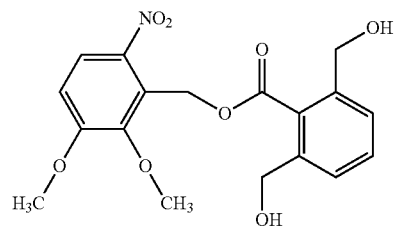

According to another embodiment, a positive photosensitive resin composition includes (A) a hydroxy group-containing alkali soluble resin; (B) the ortho-nitrobenzyl ester compound of Chemical Formula 1; (C) a photosensitive diazoquinone compound; (D) a silane compound; (E) a phenol compound; and (F) a solvent.

The hydroxy group-containing alkali soluble resin may include a polybenzoxazole precursor including a repeating unit represented by the following Chemical Formula 5, a novolac resin including a repeating unit represented by the following Chemical Formula 6, a poly-4-hydroxy styrene resin including a repeating unit represented by the following Chemical Formula 7, or a combination thereof.

[Chemical Formula 5]

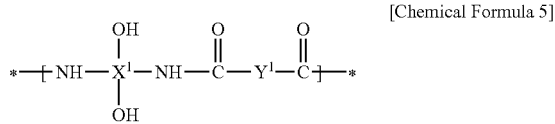

In Chemical Formula 5, $X^1$ is the same or different in each repeating unit and each $X^1$ is independently an aromatic organic group, and $Y^1$ is the same or different in each repeating unit and each $Y^1$ is independently an aromatic organic group or a divalent to hexavalent alicyclic organic group.

[Chemical Formula 6]

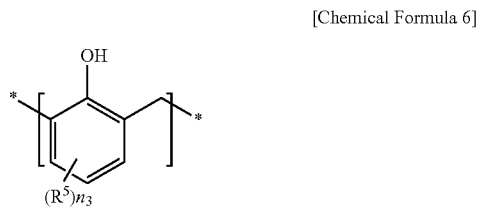

In Chemical Formula 6, each $R^5$ is the same or different and each is independently hydrogen or C1 to C10 alkyl, and $n_3$ is an integer ranging from 0 to 3.

[Chemical Formula 7]

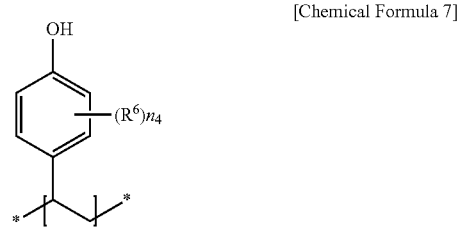

In Chemical Formula 7, each $R^6$ is the same or different and each is independently hydrogen or C1 to C10 alkyl, and $n_4$ is an integer ranging from 0 to 4.

The hydroxy group-containing alkali soluble resin may have a weight average molecular weight (Mw) of about 3,000 to about 300,000.

The resin composition may include about 0.1 to about 20 parts by weight of the ortho-nitrobenzyl ester compound (B); about 5 to about 100 parts by weight of the photosensitive diazoquinone compound (C); about 0.1 to about 30 parts by weight of the silane compound (D); about 1 to about 30 parts by weight of the phenol compound (E); and about 200 to about 900 parts by weight of the solvent (F) based on 100 parts by weight of the hydroxy group-containing alkali soluble resin (A).

According to yet another embodiment, a photosensitive resin film fabricated using the positive photosensitive resin composition is provided.

According to still another embodiment, a semiconductor device including the photosensitive resin film is provided.

Hereinafter, further embodiments will be described in detail.

The ortho-nitrobenzyl ester compound according to one embodiment can have excellent dissolution inhibition capability for the hydroxy group-containing alkali soluble resin in non-exposed parts, and may be subject to photodissolution to suppress dissolution inhibition or to promote dissolution of the hydroxy group-containing alkali soluble resin in exposed parts. The positive photosensitive resin composition including the ortho-nitrobenzyl ester compound may have excellent sensitivity, resolution, pattern profile, and residue removal properties.

DETAILED DESCRIPTION

The present invention will be described more fully hereinafter in the following detailed description of the invention, in which some but not all embodiments of the invention are described. Indeed, this invention may be embodied in many different forms and should not be construed as limited to the embodiments set forth herein; rather, these embodiments are provided so that this disclosure will satisfy applicable legal requirements.

As used herein, when a specific definition is not otherwise provided, the term "substituted" refers to one substituted with at least a substituent including halogen (F, Br, Cl or I), hydroxy, nitro, cyano, amino ($NH_2$, $NH(R^{100})$ or $N(R^{101})(R^{102})$, wherein $R^{100}$, $R^{101}$ and $R^{102}$ are the same or different and are independently C1 to C10 alkyl), amidino, hydrazine, hydrazone, carboxyl, substituted or unsubstituted alkyl, substituted or unsubstituted haloalkyl, substituted or unsubstituted alkoxy, substituted or unsubstituted alicyclic organic group, substituted or unsubstituted aryl, substituted or unsubstituted alkenyl, substituted or unsubstituted alkynyl, substituted or unsubstituted heteroaryl, substituted or unsubstituted heterocycloalkyl, or a combination thereof, in place of at least one hydrogen of a functional group.

As used herein, when a specific definition is not otherwise provided, the term "alkyl" may refer to C1 to C30 alkyl, for example C1 to C15 alkyl, the term "cycloalkyl" may refer to C3 to C30 cycloalkyl, for example C3 to C18 cycloalkyl, the term "heterocycloalkyl" may refer to C2 to C30 heterocycloalkyl, for example C2 to C18 heterocycloalkyl, the term "alkenyl" may refer to C2 to C30 alkenyl, for example C2 to C18 alkenyl, the term "alkynyl" may refer to C2 to C30 alkynyl, for example C2 to C18 alkynyl, the term "alkylene" may refer to C1 to C30 alkylene, for example C1 to C18 alkylene, the term "alkoxy" may refer to C1 to C30 alkoxy, for example C1 to C18 alkoxy, the term "cycloalkylene" may refer to C3 to C30 cycloalkylene, for example C3 to C18 cycloalkylene, the term "heterocycloalkylene" may refer to C2 to C30 heterocycloalkylene, for example C2 to C18 heterocycloalkylene, the term "aryl" may refer to C6 to C30 aryl, for example C6 to C18 aryl, the term "heteroaryl" may refer to C2 to C30 heteroaryl, for example C2 to C18 heteroaryl, the term "arylene" may refer to C6 to C30 arylene, for example C6 to C18 arylene, the term "heteroarylene" may refer to C2 to C30 heteroarylene, for example C2 to C18 heteroarylene, the term "alkylaryl" may refer to C7 to C30 alkylaryl, for example C7 to C20 alkylaryl, and the term "halogen" may refer to F, Cl, Br or I.

As used herein, when a specific definition is not otherwise provided, the terms heterocycloalkyl, heterocycloalkylene, heteroaryl, and heteroarylene may each refer to cycloalkyl, cycloalkylene, aryl, and arylene, respectively, including 1 to 3 heteroatoms including N, O, S, Si, P, or a combination thereof in place of one or more carbon ring atoms.

As used herein, when a specific definition is not otherwise provided, the term "aliphatic organic group" may refer to C1 to C30 alkyl, C2 to C30 alkenyl, C2 to C30 alkynyl, C1 to C30 alkylene, C2 to C30 alkenylene, or C2 to C30 alkynylene, for example C1 to C15 alkyl, C2 to C15 alkenyl, C2 to C15 alkynyl, C1 to C15 alkylene, C2 to C15 alkenylene, or C2 to C15 alkynylene, the term "alicyclic organic group" may refer to C3 to C30 cycloalkyl, C3 to C30 cycloalkenyl, C3 to C30 cycloalkynyl, C3 to C30 cycloalkylene, C3 to C30 cycloalkenylene, or C3 to C30 cycloalkynylene, for example C3 to C15 cycloalkyl, C3 to C15 cycloalkenyl, C3 to C15 cycloalkynyl, C3 to C15 cycloalkylene, C3 to C15 cycloalkenylene, or C3 to C15 cycloalkynylene, the term "aromatic organic group" may refer to C6 to C30 aryl, C2 to C30 heteroaryl, C6 to C30 arylene, or C2 to C30 heteroarylene, for example C6 to C16 aryl, C2 to C16 heteroaryl, C6 to C16 arylene, or C2 to C16 heteroarylene.

As used herein, when a specific definition is not otherwise provided, the term "combination" refers to mixing or copolymerization. Also, the term "copolymerization" refers to block copolymerization or random copolymerization, and the term "copolymer" refers to a block copolymer or a random copolymer.

Also, "*" refers to a linking part between the same or different atoms, or chemical formulae.

According to one embodiment, an ortho-nitrobenzyl ester compound including a compound represented by the following Chemical Formula 1 is provided.

[Chemical Formula 1]

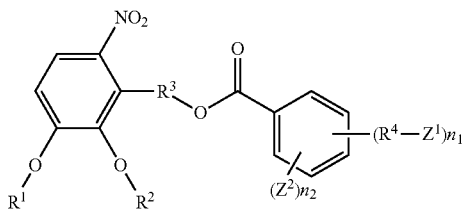

In Chemical Formula 1, $R^1$ and $R^2$ are the same or different and are each independently a substituted or unsubstituted C1 to C20 aliphatic organic group or a substituted or unsubstituted C3 to C20 alicyclic organic group, for example a substituted or unsubstituted C1 to C10 aliphatic organic group or a substituted or unsubstituted C3 to C10 alicyclic organic group, and as another example a substituted or unsubstituted C1 to C5 aliphatic organic group, or a substituted or unsubstituted C3 to C10 alicyclic organic group. For example, the aliphatic organic group may be an alkyl group.

$R^3$ and $R^4$ are the same or different and are each independently a single bond or a substituted or unsubstituted divalent C1 to C20 aliphatic organic group, for example a substituted or unsubstituted divalent C1 to C10 aliphatic organic group, and as another example a substituted or unsubstituted divalent C1 to C5 aliphatic organic group. For example, the divalent aliphatic organic group may be an alkylene group. When $R^3$ is a divalent organic group as above, for example a substituted or unsubstituted C1 to C5 aliphatic organic group, excellent sensitivity may be provided and excellent thermal stability and optical stability may be maintained effectively.

$Z^1$ and $Z^2$ are the same or different and are each independently hydroxy (OH), amine ($N(R^{103})(R^{104})$, wherein $R^{103}$ and $R^{104}$ are the same or different and are each independently hydrogen or a substituted or unsubstituted aliphatic organic group), carboxyl (COOH), or aldehyde (CHO). For example, $Z^1$ and $Z^2$ are the same or different and are each independently hydroxy (OH) or carboxyl (COOH), and as another example $Z^1$ and $Z^2$ are each hydroxy (OH).

$n_1$ and $n_2$ are the same or different and are each independently integers ranging from 0 to 5, and $n_1+n_2$ is an integer ranging from 1 to 5.

When $n_1$ is an integer of 2 or more, each $R^4$ may be the same or different and each $Z^1$ may be the same or different, and when $n_2$ is an integer of 2 or more, $Z^2$ may be the same or different.

The ortho-nitrobenzyl ester compound including a compound represented by Chemical Formula 1 may suppress a hydroxy group-containing alkali soluble resin from being dissolved in an alkali aqueous solution due to polarity difference.

In addition, the ortho-nitrobenzyl ester compound including a compound represented by Chemical Formula 1 has an ether group at 5- and 6-positions like —$OR^1$ and —$OR^2$. The ether group has an electron donating effect and thus leads an absorption wavelength to a long wavelength region and easily helps absorb light in a wavelength ranging from about 300 nm to about 450 nm, in particular, i-line (365 nm). When the ortho-nitrobenzyl ester compound including a compound represented by Chemical Formula 1 absorbs light and thus is dissolved, the hydroxy group-containing alkali soluble resin may be easily dissolved in an alkali aqueous solution.

Accordingly, the ortho-nitrobenzyl ester compound including a compound represented by Chemical Formula 1 may be used as a photosensitive assistant to a dissolution controlling agent in a positive photosensitive resin composition.

The ortho-nitrobenzyl ester compound may include a compound represented by the following Chemical Formulae 2 to 4, or a combination thereof, but is not limited thereto.

[Chemical Formula 2]

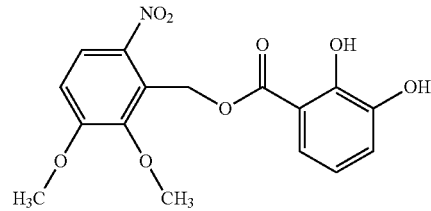

[Chemical Formula 3]

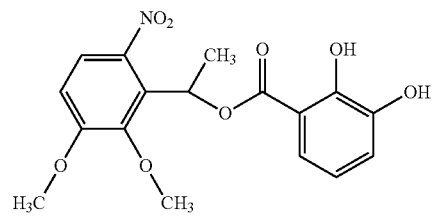

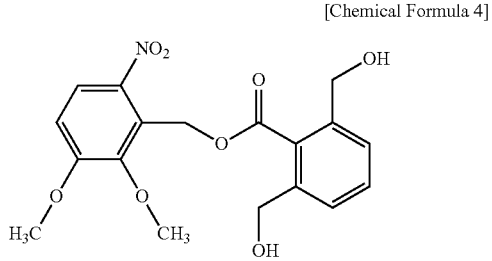

For example, the ortho-nitrobenzyl ester compound including a compound represented by the following Chemical Formula 1 may be synthesized according to the following Reaction Scheme 1, but is not limited thereto.

[Reaction Scheme 1]

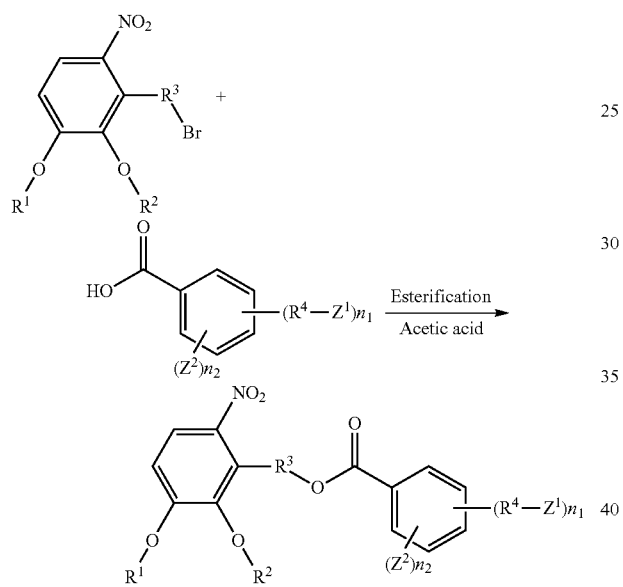

In Reaction Scheme 1, $R^1$, $R^2$, $R^3$, $R^4$, $Z^1$, $Z^2$, $n_1$, and $n_2$ are the same as defined in the above Chemical Formula 1.

According to another embodiment, a positive photosensitive resin composition includes (A) a hydroxy group-containing alkali soluble resin; (B) the ortho-nitrobenzyl ester compound; (C) a photosensitive diazoquinone compound; (D) a silane compound; (E) a phenol compound; and (F) a solvent.

The positive photosensitive resin composition may include an additional additive (G).

Hereinafter, each composition component is described in detail.

(A) Hydroxy Group-Containing Alkali Soluble Resin

The hydroxy group-containing alkali soluble resin may include a polybenzoxazole precursor including a repeating unit represented by the following Chemical Formula 5, a novolac resin including a repeating unit represented by the following Chemical Formula 6, a poly-4-hydroxy styrene resin including a repeating unit represented by the following Chemical Formula 7, or a combination thereof.

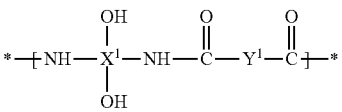

In Chemical Formula 5, $X^1$ is the same or different in each repeating unit and each $X^1$ is independently an aromatic organic group, and $Y^1$ is the same or different in each repeating unit and each $Y^1$ is independently an aromatic organic group or a divalent to hexavalent alicyclic organic group.

In Chemical Formula 6, each $R^5$ is the same or different and each is independently hydrogen or C1 to C10 alkyl, and $n_3$ is an integer ranging from 0 to 3.

Each $R^5$ may be the same or different in each repeating unit, and when $n_3$ is an integer of 2 or more, each $R^5$ may be the same or different in one repeating unit.

[Chemical Formula 7]

In Chemical Formula 7, each $R^6$ is the same or different and each is independently hydrogen or C1 to C10 alkyl, and $n_4$ is an integer ranging from 0 to 4.

Each $R^6$ may be the same or different in each repeating unit, and when $n_4$ is an integer of 2 or more, each $R^6$ may be the same or different in one repeating unit.

In Chemical Formula 5, $X^1$ is an aromatic organic group which may be a residual group derived from an aromatic diamine.

Exemplary aromatic diamines may include without limitation 3,3'-diamino-4,4'-dihydroxybiphenyl, 4,4'-diamino-3,3'-dihydroxybiphenyl, bis(3-amino-4-hydroxyphenyl)propane, bis(4-amino-3-hydroxyphenyl)propane, bis(3-amino-4-hydroxyphenyl)sulfone, bis(4-amino-3-hydroxyphenyl) sulfone, 2,2-bis(3-amino-4-hydroxyphenyl)-1,1,1,3,3,3-hexafluoropropane, 2,2-bis(4-amino-3-hydroxyphenyl)-1,1,1,3,3,3-hexafluoropropane, 2,2-bis(3-amino-4-hydroxy-5-trifluoromethylphenyl)hexafluoropropane, 2,2-bis(3-amino-4-hydroxy-6-trifluoromethylphenyl)hexafluoropropane, 2,2-bis(3-amino-4-hydroxy-2-trifluoromethylphenyl) hexafluoropropane, 2,2-bis(4-amino-3-hydroxy-5-trifluoromethylphenyl)hexafluoropropane, 2,2-bis(4-amino-3-hydroxy-6-trifluoromethylphenyl)hexafluoropropane, 2,2- bis(4-amino-3-hydroxy-2-trifluoromethylphenyl)hexafluoropropane, 2,2-bis(3-amino-4-hydroxy-5-pentafluoroethylphenyl)hexafluoropropane, 2-(3-amino-4-hydroxy-5-trifluoromethylphenyl)-2-(3-amino-4-hydroxy-5-pentafluoroethylphenyl)hexafluoropropane, 2-(3-amino-4-hydroxy-5-trifluoromethyl phenyl)-2-(3-hydroxy-4-amino-5-trifluoro methylphenyl)hexafluoropropane, 2-(3-amino-4-hydroxy-5-trifluoromethyl phenyl)-2-(3-hydroxy-4-amino-6-trifluoro methylphenyl)hexafluoropropane, 2-(3-amino-4-hydroxy-5-trifluoromethylphenyl)-2-(3-hydroxy-4-amino-2-trifluoro methylphenyl)hexafluoropropane, 2-(3-amino-4-hydroxy-2-trifluoromethyl phenyl)-2-(3-hydroxy-4-amino-5-trifluoro methylphenyl)hexafluoropropane, 2-(3-amino-4-hydroxy-6-trifluoromethyl phenyl)-2-(3-hydroxy-4-amino-5-trifluoro methylphenyl)hexafluoropropane, and the like, and combinations thereof.

$X_1$ may include a functional group represented by the following Chemical Formulae 8 and 9, but is not limited thereto.

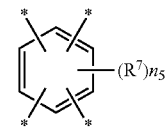

[Chemical Formula 8]

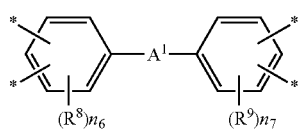

[Chemical Formula 9]

In Chemical Formulae 8 and 9, $A^1$ is O, CO, $CR^{105}R^{106}$, $SO_2$, S, or a single bond, wherein $R^{105}$ and $R^{106}$ are the same or different and are each independently hydrogen or substituted or unsubstituted alkyl, for example fluoroalkyl, $R^7$ to $R^9$ are the same or different and are each independently hydrogen, substituted or unsubstituted alkyl, hydroxyl, carboxyl, or thiol, $n_5$ is an integer of 1 or 2, $n_6$ and $n_7$ are the same or different and are independently integers ranging from 1 to 3.

In Chemical Formula 5, $Y^1$ may be an aromatic organic group, a divalent to hexavalent alicyclic organic group, a residual group of dicarboxylic acid, or a residual group of a dicarboxylic acid derivative.

Examples of the dicarboxylic acid include $Y^1(COOH)_2$ (wherein $Y^1$ is the same as $Y^1$ of Chemical Formula 5).

Examples of the dicarboxylic acid derivative include without limitation a carbonyl halide derivative of $Y^1(COOH)_2$, or an active compound of an active ester derivative obtained by reacting $Y^1(COOH)_2$ and 1-hydroxy-1,2,3-benzotriazole (wherein $Y^1$ is the same as $Y^1$ of Chemical Formula 5). Exemplary dicarboxylic acid derivatives may include without limitation 4,4'-oxydibenzoylchloride, diphenyloxydicarbonyldichloride, bis(phenylcarbonylchloride)sulfone, bis(phenylcarbonylchloride)ether, bis(phenylcarbonylchloride)phenone, phthaloyl dichloride, terephthaloyl dichloride, isophthaloyl dichloride, dicarbonyldichloride, diphenyloxydicarboxylatedibenzotriazole, and the like, and combinations thereof.

$Y^1$ may include a functional group represented by the following Chemical Formulae 10 to 12, but is not limited thereto.

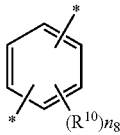

[Chemical Formula 10]

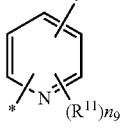

[Chemical Formula 11]

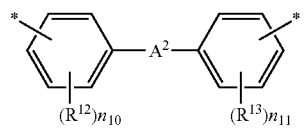

[Chemical Formula 12]

In Chemical Formulae 10 to 12, $R^{10}$ to $R^{13}$ are the same or different and are independently hydrogen or substituted or unsubstituted alkyl, $n_8$, $n_{10}$ and $n_{11}$ are integers ranging from 1 to 4, $n_9$ is an integer ranging from 1 to 3, $A^2$ is O, $CR^{107}R^{108}$, CO, CONH, S, $SO_2$, or a single bond, wherein $R^{107}$ and $R^{108}$ are the same or different and are independently hydrogen or substituted or unsubstituted alkyl, for example fluoroalkyl.

The hydroxy group-containing alkali soluble resin may have a weight average molecular weight (Mw) of about 3,000 to about 300,000. When the hydroxy group-containing alkali soluble resin has a weight average molecular weight within the above range, it may have a sufficient residual film ratio in a non-exposed part during the development of an alkali aqueous solution, which can provide efficient patterning.

(B) Ortho-Nitrobenzyl Ester Compound

An ortho-nitrobenzyl ester compound may include a compound represented by the above Chemical Formula 1. In exemplary embodiments, the ortho-nitrobenzyl ester compound may include a compound represented by the above Chemical Formulae 2 to 4 or a combination thereof but is not limited thereto.

The ortho-nitrobenzyl ester compound may suppress dissolution of the hydroxy group-containing alkali soluble resin in the non-exposed part. On the other hand, since the ortho-nitrobenzyl ester compound is dissolved in the exposed part, the hydroxy group-containing alkali soluble resin may be easily dissolved, improving sensitivity. Accordingly, when the ortho-nitrobenzyl ester compound is used as a photosensitive assistant or a dissolution controlling agent, it may accomplish efficient and optional patterning.

In addition, since the ortho-nitrobenzyl ester compound is cross-linked or polymerized by heating, it may minimize or prevent softness of a film during the curing at about 200° C. or lower, which can improve mechanical properties, chemical resistance, and flux resistance. When $n_1$ is 2 or more in Chemical Formula 1, it may further effectively improve mechanical properties, chemical resistance, and flux resistance.

In the positive photosensitive resin composition, the ortho-nitrobenzyl ester compound may be included in an amount ranging from about 0.1 to about 20 parts by weight, for example about 0.1 to about 10 parts by weight, as another example about 0.1 to about 5 parts by weight, as another example about 0.5 to about 5 parts by weight, and as another example about 1 to about 3 parts by weight, based on 100 parts by weight of the hydroxy group-containing alkali soluble resin. In some embodiments, the positive photosensitive resin composition may include the ortho-nitrobenzyl ester compound in an amount of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20 parts by weight. Further, according to some embodiments, the amount of the ortho-nitrobenzyl ester compound can be in a range from about any of the foregoing amounts to about any other of the foregoing amounts.

When the ortho-nitrobenzyl ester compound is included in an amount within the above range, dissolution of a non-exposed part may be effectively inhibited. In addition, the ortho-nitrobenzyl ester compound with the following photosensitive diazoquinone compound may efficiently absorb light in an exposed part and thus can be dissolved, which can help dissolution of the hydroxy group-containing alkali soluble resin. Accordingly, a pattern may be well formed without a residue by exposure and without loss of film thickness during the development. As a result, the ortho-nitrobenzyl ester compound may function as a photosensitive assistant or a dissolution controlling agent, for example, as a dissolution inhibiting agent.

(C) Photosensitive Diazoquinone Compound

The photosensitive diazoquinone compound may be a compound including a 1,2-benzoquinone diazide or 1,2-naphtoquinone diazide structure.

The photosensitive diazoquinone compound may include a compound represented by the following Chemical Formulae 13 and 15 to 17, or a combination thereof, but is not limited thereto.

[Chemcial Formula 13]

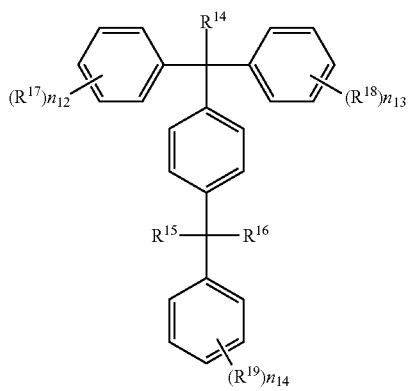

In Chemical Formula 13,
$R^{14}$ to $R^{16}$ are the same or different and are independently hydrogen or substituted or unsubstituted alkyl, for example $CH_3$,
$R^{17}$ to $R^{19}$ are the same or different and are independently OQ, wherein Q is hydrogen, the following Chemical Formula 14a or Chemical Formula 14b, provided that all Qs are not simultaneously hydrogen, and
$n_{12}$ to $n_{14}$ are each independently integers ranging from 1 to 3.

[Chemical Formula 14a]

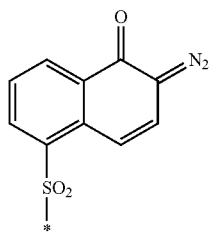

[Chemical Formula 14b]

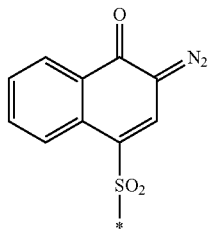

[Chemical Formula 15]

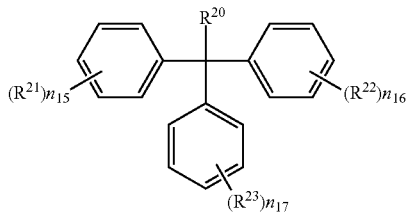

In Chemical Formula 15,
$R^{20}$ is hydrogen or substituted or unsubstituted alkyl,
$R^{21}$ to $R^{23}$ are OQ, wherein Q is the same as defined in the above Chemical Formula 13, and
$n_{15}$ to $n_{17}$ are each independently integers ranging from 1 to 3.

[Chemical Formula 16]

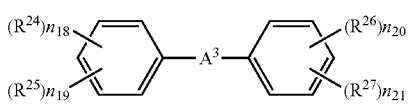

In Chemical Formula 16,
$A^3$ is CO or $CR^{109}R^{110}$, wherein $R^{109}$ and $R^{110}$ are the same or different and are independently substituted or unsubstituted alkyl,
$R^{24}$ to $R^{27}$ are the same or different and are independently hydrogen, substituted or unsubstituted alkyl, OQ, or NHQ, wherein Q is the same as defined in the above Chemical Formula 13,
$n_{18}$ to $n_{21}$ are independently integers ranging from 1 to 4, and
$n_{18}+n_{19}$ and $n_{20}+n_{21}$ are independently integers of 5 or less, provided that at least one of $R^{24}$ and $R^{25}$ is OQ, and one aromatic ring includes one to three OQs and the other aromatic ring includes one to four OQs.

[Chemical Formula 17]

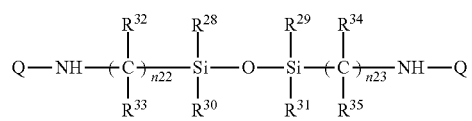

In Chemical Formula 17,
$R^{28}$ to $R^{35}$ are the same or different and are each independently hydrogen or substituted or unsubstituted alkyl,
$n_{22}$ and $n_{23}$ are each independently integers ranging from 1 to 5, and
Q is the same as defined in the above Chemical Formula 13.

In the positive photosensitive resin composition, the photosensitive diazoquinone compound may be included in an amount of about 5 to about 100 parts by weight, based on 100 parts by weight of the hydroxy group-containing alkali soluble resin. In some embodiments, the positive photosensitive resin composition may include the photosensitive diazoquinone compound in an amount of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 48, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 parts by weight. Further, according to some embodiments, the amount of the photosensitive diazoquinone compound can be in a range from about any of the foregoing amounts to about any other of the foregoing amounts.

When the amount of the photosensitive diazoquinone compound is within the above range, the pattern may be well-formed without a residue from exposure, and a film thickness loss during development can be minimized or prevented which can provide a good pattern.

(D) Silane Compound

The silane compound improves adherence between the photosensitive resin composition and a substrate and adherence between an epoxy molding compound (EMC) positioned on the photosensitive resin film in a subsequent semiconductor manufacturing process and the photosensitive resin film.

Exemplary silane compounds may include without limitation a compounds represented by the following Chemical Formulae 18 to 20; silane compounds including a carbon-carbon unsaturated bond such as vinyltrimethoxysilane, vinyltriethoxysilane, vinyltrichlorosilane, and vinyltris(β-methoxyethoxy)silane; 3-methacryloxypropyltrimethoxysilane, 3-acryloxypropyltrimethoxysilane, p-styryltrimethoxysilane, 3-methacryloxypropylmethyldimethoxysilane, and 3-methacryloxypropylmethyldiethoxysilane; trimethoxy[3-(phenylamino)propyl]silane, and the like, and combinations thereof.

[Chemical Formula 18]

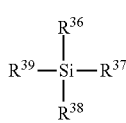

In Chemical Formula 18, $R^{36}$ is a vinyl group, substituted or unsubstituted alkyl, or substituted or unsubstituted aryl, for example 3-(metha)cryloxypropyl, p-styryl, or 3-(phenylamino)propyl $R^{37}$ to $R^{39}$ are the same or different and are independently substituted or unsubstituted alkoxy, substituted or unsubstituted alkyl, or halogen, provided that at least one of $R^{37}$ to $R^{39}$ is alkoxy or halogen. The alkoxy may be C1 to C8 alkoxy, and the alkyl may be C1 to C20 alkyl.

[Chemical Formula 19]

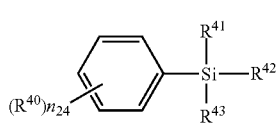

In Chemical Formula 19, $R^{40}$ are the same or different and are each independently $NH_2$ or $CH_3CONH$, $R^{41}$ to $R^{43}$ are the same or different and are each independently substituted or unsubstituted alkoxy, for example $OCH_3$ or $OCH_2CH_3$, and $n_{24}$ is an integer ranging from 1 to 5.

[Chemical Formula 20]

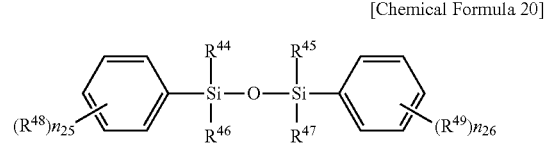

In Chemical Formula 20, $R^{44}$ to $R^{47}$ are the same or different and are each independently substituted or unsubstituted alkyl or substituted or unsubstituted alkoxy, for example $CH_3$ or $OCH_3$, $R^{48}$ and $R^{49}$ are the same or different and are each independently substituted or unsubstituted amino, for example $NH_2$ or $CH_3CONH$, and $n_{25}$ and $n_{26}$ are each independently integers ranging from 1 to 5.

The positive photosensitive resin composition may include the silane compound in an amount of about 0.1 to about 30 parts by weight, based on 100 parts by weight of the hydroxy group-containing alkali soluble resin. In some embodiments, the positive photosensitive resin composition may include the silane compound in an amount of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 parts by weight. Further, according to some embodiments, the amount of the silane compound can be in a range from about any of the foregoing amounts to about any other of the foregoing amounts.

When the silane compound is included in an amount within the above range, adherence between lower and upper layers may be sufficiently improved, residue film may not remain after development, and optical properties (transmittance) and mechanical properties such as tensile strength, elongation, and Young's modulus may be improved.

(E) Phenol Compound

The phenol compound increases dissolution rate and sensitivity of exposure parts during development using an alkali aqueous solution to form a pattern using a photosensitive resin composition, and plays a role of forming high resolution patterns without residues.

Exemplary phenol compounds include without limitation compounds represented by the following Chemical Formulae 21 to 26, and combinations thereof.

[Chemical Formula 21]

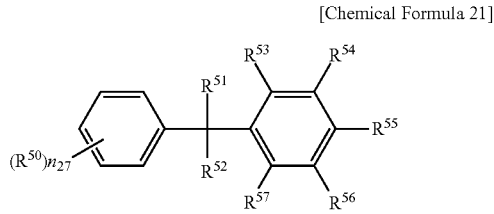

In Chemical Formula 21, $R^{50}$ to $R^{52}$ are the same or different and are each independently hydrogen or substituted or unsubstituted alkyl, $R^{53}$ to $R^{57}$ are the same or different and are each independently H, OH, or substituted or unsubstituted alkyl, for example $CH_3$, and $n_{27}$ is an integer ranging from 1 to 5.

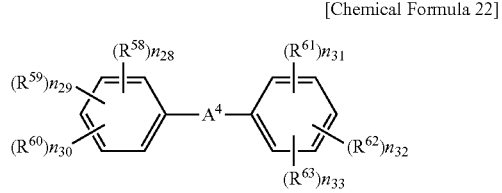

[Chemical Formula 22]

In Chemical Formula 22, $R^{58}$ to $R^{63}$ are the same or different and are each independently H, OH, or substituted or unsubstituted alkyl, $A^4$ is $CR^{111}R^{112}$ or a single bond, wherein $R^{111}$ and $R^{112}$ are the same or different and are each independently hydrogen or substituted or unsubstituted alkyl, for example $CH_3$, and $n_{28}+n_{29}+n_{30}$ and $n_{31}+n_{32}+n_{33}$ are each independently integers of 5 or less.

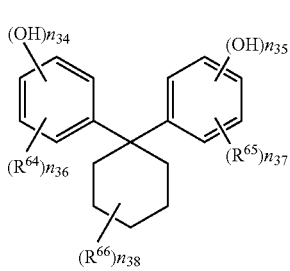

[Chemical Formula 23]

In Chemical Formula 23, $R^{64}$ to $R^{66}$ are the same or different and are each independently hydrogen or substituted or unsubstituted alkyl, $n_{34}$, $n_{35}$ and $n_{38}$ are each independently integers of 1 to 5, and $n_{36}$ and $n_{37}$ are each independently integers of 0 to 4.

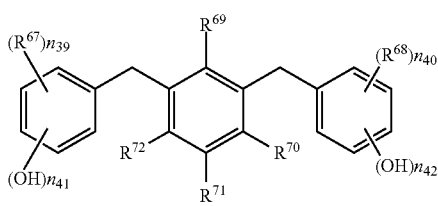

[Chemical Formula 24]

In Chemical Formula 24, $R^{67}$ to $R^{72}$ are the same or different and are each independently hydrogen, OH, or substituted or unsubstituted alkyl, $n_{39}$ to $n_{42}$ are each independently integers of 1 to 4, and provided that $n_{39}+n_{41}$ and $n_{40}+n_{42}$ are each independently integers of 5 or less.

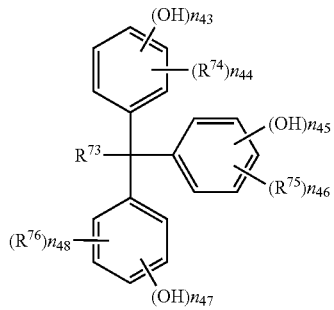

[Chemical Formula 25]

In Chemical Formula 25, $R^{73}$ is substituted or unsubstituted alkyl, for example $CH_3$, $R^{74}$ to $R^{76}$ are the same or different and are each independently hydrogen or substituted or unsubstituted alkyl, $n_{43}$, $n_{45}$ and $n_{47}$ are each independently integers of 1 to 5, $n_{44}$, $n_{46}$ and $n_{48}$ are each independently integers of 0 to 4, and provided that $n_{43}+n_{44}$, $n_{45}+n_{46}$ and $n_{47}+n_{48}$ are each independently integers of 5 or less.

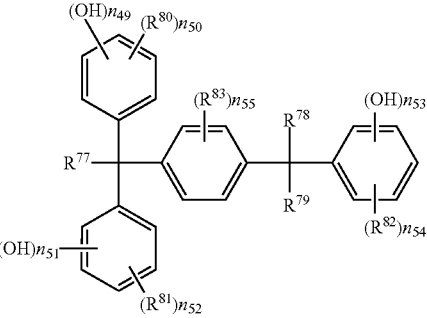

[Chemical Formula 26]

In Chemical Formula 26, $R^{77}$ to $R^{79}$ are the same or different and are each independently substituted or unsubstituted alkyl, for example $CH_3$, $R^{80}$ to $R^{83}$ are the same or different and are each independently hydrogen or substituted or unsubstituted alkyl, $n_{49}$, $n_{51}$ and $n_{53}$ are each independently integers of 1 to 5, $n_{50}$, $n_{52}$ and $n_{54}$ are each independently integers of 0 to 4, and, $n_{55}$ is an integer of 1 to 4, and, provided that $n_{49}+n_{50}$, $n_{51}+n_{52}$ and $n_{53}+n_{54}$ are each independently integers of 5 or less.

Exemplary phenol compounds include without limitation 2,6-dimethoxymethyl-4-t-butyl phenol, 2,6-dimethoxymethyl-p-cresol, 2,6-diacetoxymethyl-p-cresol, and the like, and combinations thereof.

The positive photosensitive resin composition may include the phenol compound in an amount of about 1 to about 30 parts by weight, based on 100 parts by weight of the hydroxy group-containing alkali soluble resin. In some embodiments, the positive photosensitive resin composition may include the phenol compound in an amount of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 parts by weight. Further, according to some embodiments, the amount of the phenol compound can be in a range from about any of the foregoing amounts to about any other of the foregoing amounts.

When the phenol compound is included in an amount within the above range, sensitivity during development may not decrease, and the dissolution rate of the non-exposed part may be suitably increased to provide a good pattern. In addition, precipitation during freezing may be minimized or eliminated to provide excellent storage stability.

(F) Solvent

The positive photosensitive resin composition includes a solvent that can dissolve each component easily.

Examples of the solvent include without limitation N-methyl-2-pyrrolidone, γ-butyrolactone, N,N-dimethyl acetamide, dimethylsulfoxide, diethyleneglycoldimethylether, diethyleneglycoldiethylether, diethyleneglycoldibutylether, propyleneglycolmonomethylether, dipropyleneglycolmonomethylether, propyleneglycolmonomethyletheracetate, methyllactate, ethyllactate, butyllactate, methyl-1,3-butyleneglycolacetate, 1,3-butyleneglycol-3-monomethylether, methyl pyruvate, ethyl pyruvate, methyl-3-methoxy propionate and the like, and combination thereofs. The solvent may be used singularly or in combination.

The positive photosensitive resin composition may include the solvent in an amount of about 200 to about 900 parts by weight, based on 100 parts by weight of the hydroxy group-containing alkali soluble resin. In some embodiments, the positive photosensitive resin composition may include the solvent in an amount of 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, or 900 parts by weight. Further, according to some embodiments, the amount of the solvent can be in a range from about any of the foregoing amounts to about any other of the foregoing amounts.

When the solvent is used in an amount within the above range, a sufficiently thick film can be obtained, and good solubility and coating can be provided.

(G) Other Additive(s)

The positive photosensitive resin composition according to one embodiment may further include other additives (G).

The other additive can includes a latent thermal acid generator. Exemplary latent thermal acid generators include without limitation arylsulfonic acids, such as p-toluenesulfonic acid, and a benzenesulfonic acid; perfluoroalkylsulfonic acids, such as trifluoromethanesulfonic acid, and trifluorobutanesulfonic acid; alkylsulfonic acids, such as methanesulfonic acid, ethanesulfonic acid, and butanesulfonic acid; and the like; and combinations thereof.

The latent thermal acid generator is a catalyst for the dehydration reaction of the phenol type hydroxyl group-contained polyamide of the polybenzoxazole precursor and cyclization reaction, and thus a cyclization reaction can be performed smoothly even if curing temperature is decreased.

In addition, the positive photosensitive resin composition may further include a suitable surfactant or leveling agent to prevent staining of the film or to improve development.

The process for forming a pattern using a positive photosensitive resin composition includes: coating a positive photosensitive resin composition on a supporting substrate; drying the coated positive photosensitive resin composition to provide a positive photosensitive resin composition layer; exposing the positive photosensitive resin composition layer; developing the exposed positive photosensitive resin composition layer in an alkali aqueous solution to provide a photosensitive resin film; and heating the photosensitive resin film. The conditions of processes to provide a pattern are widely known in this art, so detailed descriptions thereof will be omitted in this specification.

According to another embodiment, a photosensitive resin film fabricated using the positive photosensitive resin composition is provided. The photosensitive resin film may be used as an insulation layer and/or a protective layer.

According to further another embodiment, a semiconductor device including the photosensitive resin film is provided. The photosensitive resin composition according to the present embodiment can be used as an insulation layer, a passivation layer, and/or a buffer coating layer in a semiconductor device. The positive photosensitive resin composition may also be used to form a surface protective layer and/and an interlayer insulating layer of a semiconductor device.

The following examples illustrate the present invention in more detail. However, it is understood that the present invention is not limited by these examples.

EXAMPLES

Synthesis Example 1

Synthesis of an Ortho-Nitrobenzyl Ester Compound 10 g of 5,6-dimethoxy-2-nitrobenzyl bromide and 15 g of 2,3-dihydroxy benzoic acid are placed in a 4-necked flask equipped with an agitator, a thermostat, a nitrogen gas injector, and a cooler while nitrogen was passed therethrough, and 100 ml of acetic acid is added thereto to prepare a mixed solution. The mixed solution is blocked from ultraviolet (UV) and agitated at 3° C. for 24 hours. Then, the reactant is precipitated in methanol. The precipitate is filtered under a reduced pressure, several times washed with methanol at 0° C., and dried under vacuum at 40° C. for 17 hours, obtaining 12 g of a yellow solid compound represented by the following Chemical Formula 2.

[Chemical Formula 2]

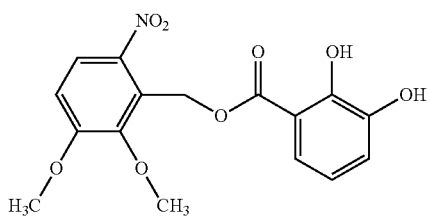

Synthesis Example 2

Synthesis of an Ortho-Nitrobenzyl Ester Compound 10 g of 5,6-dimethoxy-2-nitrobenzyl bromide and 12 g of 2,6-dimethylol benzoic acid are placed in a 4-necked flask with an agitator, a thermostat, a nitrogen gas injector, and a cooler while nitrogen is passed through the flask, and 100 ml of acetic acid is added thereto, preparing a mixed solution. The mixed solution is blocked from ultraviolet (UV) and agitated at 3° C. for 24 hours. Then, the agitated product is precipitated in methanol. Next, the precipitate is filtered under a reduced pressure, washed several times with 0° C. methanol, and dried under vacuum at 40° C. for 17 hours, obtaining 8 g of a yellow solid compound represented by the following Chemical Formula 4.

[Chemical Formula 4]

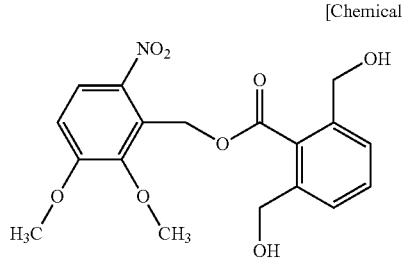

Example 1

Preparation of a Positive Photosensitive Resin Composition 18.3 g of 2,2-bis(3-amino-4-hydroxyphenyl)-1,1,1,3,3,3-hexafluoro propane and 13.3 g of 4,4'-oxydibenzoylchloride are used with pyridine as a catalyst under an N-methyl-2-pyrrolidone (NMP) solvent to prepare an alkali soluble resin for a positive photosensitive resin composition. 15 g of the alkali soluble resin is dissolved in 35.0 g of γ-butyrolactone (GBL). Then, 3 g of a photosensitive diazoquinone represented by the following Chemical Formula 27, 1 g of a phenol compound represented by Chemical Formula 28, 0.4 g of a silane compound represented by Chemical Formula 29, and 0.15 g of a compound represented by the above Chemical Formula 2 are added to the solution and dissolved therein. The resulting solution is filtered with a 0.45 μm fluororesin filter, obtaining a positive photosensitive resin composition.

[Chemical Formula 27]

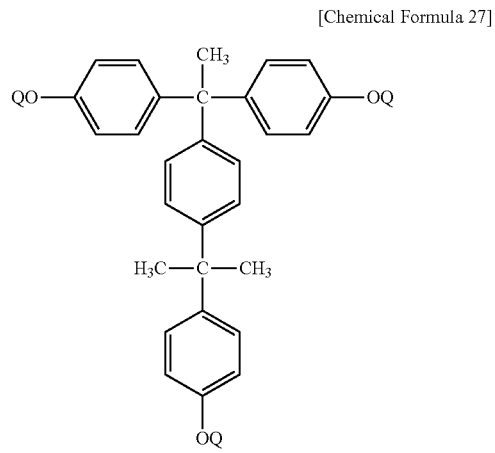

In Chemical Formula 27,

Q is the same as defined in the above Chemical Formula 13, and 67% of Q is substituted with the above Chemical Formula 14a.

[Chemical Formula 28]

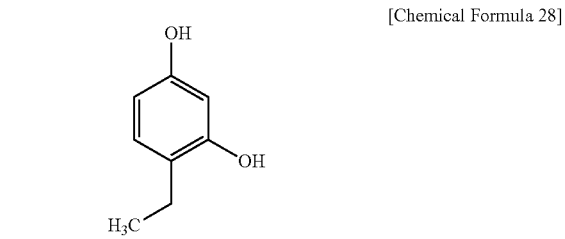

[Chemical Formula 29]

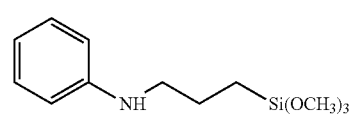

Example 2

Preparation of a Positive Photosensitive Resin Composition

A positive photosensitive resin composition is prepared according to the same method as in Example 1 except for using 0.15 g of a compound represented by the above Chemical Formula 4 instead of a compound represented by the above Chemical Formula 2.

Example 3

Preparation of a Positive Photosensitive Resin Composition

A positive photosensitive resin composition is prepared according to the same method as in Example 1 except for using 0.3 g of a compound represented by the above Chemical Formula 2.

Example 4

Preparation of a Positive Photosensitive Resin Composition

A positive photosensitive resin composition is prepared according to the same method as in Example 1 except for using 0.3 g of a compound represented by the above Chemical Formula 4 instead of a compound represented by the above Chemical Formula 2.

Example 5

Preparation of a Positive Photosensitive Resin Composition

A positive photosensitive resin composition is prepared according to the same method as in Example 1 except for using 1.5 g of a compound represented by the above Chemical Formula 2.

Example 6

Preparation of a Positive Photosensitive Resin Composition

A positive photosensitive resin composition is prepared according to the same method as in Example 1 except for using 1.5 g of a compound represented by the above Chemical Formula 4 instead of a compound represented by the above Chemical Formula 2.

Comparative Example 1

Preparation of a Positive Photosensitive Resin Composition

A positive photosensitive resin composition is prepared according to the same method as in Example 1 except for using no compound represented by the above Chemical Formula 2.

Experimental Example 1

Sensitivity, Resolution, and Residual Film Ratio Evaluations

Each positive photosensitive resin composition prepared from Examples 1 to 6 and Comparative Example 1 are coated on a 8-inch wafer by a spin coater manufactured by Mikasa (1H-DX2), then heated on a hot plate at 120° C. for 4 minutes to provide a photosensitive polybenzoxazole precursor film.

The photosensitive polybenzoxazole precursor film is exposed to a light for different times with a mask having variously-sized patterns by using I-line stepper (NSR i10C) made by Japanese Nikon Co., then dissolved to remove the exposed part in a 2.38 wt % tetramethylammonium hydroxide aqueous solution through 2 puddles for 60 seconds at a room temperature, and washed with pure water for 30 seconds, obtaining a pattern.

The resolution of the film pattern is examined using an optical microscope.

The film thickness change after the pre-baking and development is evaluated by measuring a coating thickness with a ST4000-DLX equipment made by K-MAC. The film thickness change is used to calculate a residual film ratio (thickness after development/thickness before development, unit: %).

The sensitivity of a photosensitive resin composition is evaluated by measuring exposure time taken until a 10 μm L/S (line and space) pattern is formed to have a line width of 1×1 after the exposure and development as an optimum exposure time.

The property evaluation results are provided in the following Table 1.

TABLE 1

| | Ortho-nitrobenzyl ester compound | Amount of ortho-nitrobenzyl ester compound (based on 100 parts by weight of alkali soluble resin) | Film thickness (μm) | | Sensitivity (mJ/cm$^2$) | Residual film ratio (%) |
|---|---|---|---|---|---|---|
| | | | prebaking | After development | | |
| Ex. 1 | Chemical Formula 2 | 1 | 10.01 | 9.20 | 300 | 91.90 |
| Ex. 2 | Chemical Formula 4 | 1 | 10.22 | 9.31 | 350 | 91.10 |
| Ex. 3 | Chemical Formula 2 | 2 | 10.04 | 9.19 | 350 | 91.53 |
| Ex. 4 | Chemical Formula 4 | 2 | 10.24 | 9.35 | 400 | 91.31 |
| Ex. 5 | Chemical Formula 2 | 10 | 10.01 | 9.33 | 450 | 93.20 |
| Ex. 6 | Chemical Formula 4 | 10 | 10.02 | 9.30 | 500 | 92.81 |
| Comp. Ex. 1 | — | — | 9.984 | 8.861 | 500 | 88.75 |

As shown in Table 1, since the positive photosensitive resin compositions according to Examples 1 to 6 brought about a higher residual film ratio than the one according to Comparative Example 1, they may form a better pattern when developed by an alkali aqueous solution.

In addition, the positive photosensitive resin composition according to Examples 1 to 6 has better or at least equivalent sensitivity than the one according to Comparative Example 1. In particular, the positive photosensitive resin compositions including an ortho-nitrobenzyl ester compound in a small amount according to Examples 1 to 4 had much better sensitivity, since it did not disturb a diazoquinone compound from absorbing light.

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

What is claimed is:

1. A positive photosensitive resin composition comprising
   (A) a novolac resin including a repeating unit represented by the following Chemical Formula 6, a poly-4-hydroxy styrene resin including a repeating unit represented by the following Chemical Formula 7, or a combination thereof;
   (B) an ortho-nitrobenzyl ester compound including a compound represented by the following Chemical Formula 1-1 or Chemical Formula 1-2;
   (C) a photosensitive diazoquinone compound;
   (D) a silane compound;
   (E) a phenol compound; and
   (F) a solvent,

[Chemical Formula 5]

$$*\!\!-\!\!\{\mathrm{NH}\!-\!\underset{\underset{\mathrm{OH}}{|}}{\overset{\overset{\mathrm{OH}}{|}}{X^1}}\!-\!\mathrm{NH}\!-\!\overset{\overset{\mathrm{O}}{\|}}{\mathrm{C}}\!-\!Y^1\!-\!\overset{\overset{\mathrm{O}}{\|}}{\mathrm{C}}\}\!\!-\!\!*$$

wherein in Chemical Formula 6,
each $R^5$ is the same or different and each is independently hydrogen or C1 to C10 alkyl, and
$n_3$ is an integer ranging from 0 to 3,

[Chemical Formula 7]

wherein in Chemical Formula 7,
each $R^6$ is the same or different and each is independently hydrogen or C1 to C10 alkyl, and
$n_4$ is an integer ranging from 0 to 4,

[Chemical Formula 1-1]

[Chemical Formula 1-2]

wherein in Chemical Formulas 1-1 and 1-2,
$R^1$ and $R^2$ are the same or different and are each independently substituted or unsubstituted C1 to C20 aliphatic organic group or substituted or unsubstituted C3 to C20 alicyclic organic group,
$R^3$ and $R^4$ are the same or different and are each independently a single bond or a substituted or unsubstituted divalent C1 to C20 aliphatic organic group,
$Z^1$ and $Z^2$ are the same or different and are each independently hydroxy (OH), amine (N($R^{103}$)($R^{104}$), wherein $R^{103}$ and $R^{104}$ are the same or different and are each independently hydrogen or a substituted or unsubstituted aliphatic organic group), carboxyl (COOH) or aldehyde (CHO),
n1 and n2 are the same or different and are each independently 0 or 1,
wherein the resin composition comprises:
about 0.1 to about 20 parts by weight of the ortho-nitrobenzyl ester compound including a compound represented by Chemical Formula 1-1 or Chemical Formula 1-2 (B);
about 5 to about 100 parts by weight of the photosensitive diazoquinone compound (C);
about 0.1 to about 30 parts by weight of the silane compound (D);
about 1 to about 30 parts by weight of the phenol compound (E); and
about 200 to about 900 parts by weight of the solvent (F),
based on 100 parts by weight of the novolac resin including a repeating unit represented by Chemical Formula 6, the poly-4-hydroxy styrene resin including a repeating unit represented by Chemical Formula 7, or a combination thereof (A).

2. The positive photosensitive resin composition of claim 1, wherein the novolac resin including a repeating unit represented by the following Chemical Formula 6, a poly-4-hydroxy styrene resin including a repeating unit represented by the following Chemical Formula 7, or a combination thereof has a weight average molecular weight (Mw) of about 3,000 to about 300,000.

3. A photosensitive resin film fabricated using the positive photosensitive resin composition according to claim 1.

4. A semiconductor device including the photosensitive resin film according to claim 3.

* * * * *

UNITED STATES PATENT AND TRADEMARK OFFICE
CERTIFICATE OF CORRECTION

PATENT NO. : 8,592,131 B2  
APPLICATION NO. : 13/239441  
DATED : November 26, 2013  
INVENTOR(S) : Chung et al.

Page 1 of 1

It is certified that error appears in the above-identified patent and that said Letters Patent is hereby corrected as shown below:

On the Title Page

Item (73) the Assignee reads: Cheil Industries Inc., Gumi-si (KR) and should read:

Cheil Industries Inc., Gumi-si (KR) and Samsung Electronics Co., Ltd., Suwon-si (KR)

In the Claims

Claim 1, Column 23, Lines 39-44 read:

[Chemical Formula 5]

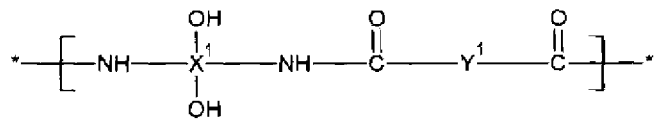

and should read:

[Chemical Formula 6]

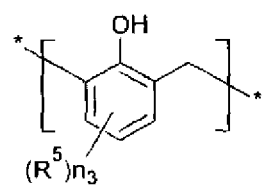

Signed and Sealed this  
Fifteenth Day of April, 2014

Michelle K. Lee  
*Deputy Director of the United States Patent and Trademark Office*